(12) United States Patent
Shalon et al.

(10) Patent No.: US 6,309,891 B1
(45) Date of Patent: Oct. 30, 2001

(54) CAPILLARY PRINTING SYSTEMS

(75) Inventors: Tidhar D. Shalon, Atherton; Joseph R. Maurino, Belmont; Loren D. Titsworth, Fremont; JoeBen Bevirt, Palo Alto, all of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/150,502

(22) Filed: Sep. 9, 1998

(51) Int. Cl.[7] .................................................. B01L 3/02
(52) U.S. Cl. ...................... 436/180; 73/864.01; 101/494; 141/31; 422/100; 436/49; 436/54; 436/176
(58) Field of Search ................................. 422/63, 65, 81, 422/100, 103, 104; 436/43, 49, 54, 174, 180, 176; 73/864.01, 864.24, 864.25; 141/31; 101/494

(56) References Cited

U.S. PATENT DOCUMENTS

| | | | |
|---|---|---|---|
| 4,106,911 | * | 8/1978 | Marcelli ................................. 141/237 |
| 4,142,656 | | 3/1979 | Smith et al. . |
| 4,334,879 | * | 6/1982 | Fujimori .................................. 422/99 |
| 4,441,532 | | 4/1984 | Darougar . |
| 4,461,328 | * | 7/1984 | Kenney .................................. 141/67 |
| 4,478,094 | * | 10/1984 | Salomaa et al. ................... 73/863.32 |
| 4,498,510 | * | 2/1985 | Minshew, Jr. et al. ................ 141/27 |
| 4,511,534 | * | 4/1985 | Bennett, Jr. et al. . |
| 4,699,884 | * | 10/1987 | Noss et al. ........................... 435/287 |
| 4,731,335 | * | 3/1988 | Brigati ................................. 436/180 |
| 4,844,298 | * | 7/1989 | Ohaka et al. ........................... 222/58 |
| 4,975,250 | * | 12/1990 | Mordecki ............................... 422/99 |
| 5,000,921 | * | 3/1991 | Hanaway et al. ..................... 422/100 |
| 5,026,526 | * | 6/1991 | Quenin et al. . |
| 5,189,787 | * | 3/1993 | Reed et al. . |
| 5,262,128 | * | 11/1993 | Leighton et al. ..................... 422/100 |
| 5,338,688 | * | 8/1994 | Deeg et al. ........................... 436/180 |
| 5,343,909 | * | 9/1994 | Goodman ............................. 141/242 |
| 5,440,940 | * | 8/1995 | Wilkins ............................. 73/864.16 |
| 5,544,535 | * | 8/1996 | Thomas . |
| 5,551,487 | * | 9/1996 | Gordon et al. ........................... 141/1 |
| 5,736,105 | * | 4/1998 | Astle .................................... 422/100 |
| 5,741,554 | * | 4/1998 | Tisone .................................. 427/424 |
| 5,763,278 | * | 6/1998 | Sickinger et al. .................... 436/180 |
| 5,770,151 | * | 6/1998 | Roach et al. ........................... 422/63 |
| 5,807,522 | * | 9/1998 | Brown et al. .......................... 422/50 |
| 5,867,187 | * | 2/1999 | Toniolo . |
| 5,882,930 | * | 3/1999 | Baier ..................................... 436/49 |
| 6,062,390 | * | 5/2000 | Nakamura . |

FOREIGN PATENT DOCUMENTS

| | | |
|---|---|---|
| 89 10192 | 11/1989 | (WO) . |
| 98/29736 | 7/1998 | (WO) . |

* cited by examiner

Primary Examiner—Jan Ludlow
(74) Attorney, Agent, or Firm—Richard Aron Osman (57) ABSTRACT

The invention provides printing systems and methods for depositing small volumes of liquid on solid substrates. These systems and methods are useful with a wide variety of liquids and substrates and offer a wide variety of applications, including the deposition of arrays of analytes. In particular embodiments, the systems comprise a preservation device, a detachable ganged plurality of printing devices, and/or a wire bonding capillary.

41 Claims, 9 Drawing Sheets

CAPILLARY PRINTING SYSTEMS

INTRODUCTION

1. Field of the Invention

The invention is in the field of capillary printing systems and their fabrication.

2. Background

The accurate dispensing and deposition on a substrate of small volumes of liquid has been effected with a variety of printing instruments including micropipettes and injectors (see, e.g. U.S. Pat. Nos. 4,815,325; 5,601,980; 5,747,102), ink-jet printers (see, e.g. U.S. Pat No. 5,338,688), and fountain-pen type contact-deposition capillaries (see, e.g. WO95/35505 and U.S. Pat. No. 5,770,151). In addition, a number of multiport liquid transfer and delivery apparatuses are commercially available (e.g. MICROLAB® DNA Workstation by Hamilton Co., Reno Nev.; HYDRA Microdispenser by Robbins Scientific, Sunnyvale Calif.; Microarray Printing System by Genometrix, The Woodlands, Tex.). While some of these instruments have been used to print ordered analytical or probe arrays, they offer various relative advantages and disadvantages, including differing print resolution, speed, cross-contamination control, probe tolerances, etc. For example, the cartridges utilized in ink-jet printers dispense a controlled volume of liquid by use of a pressure wave created within the cartridge and which results from a sharp temperature increase to the ink that can damage or sheer a molecularly fragile probe. Existing pipettors and contact deposition capillaries are better suited to printing fragile probes but require washings between different probe loadings and offer limited print resolution. The present invention provides improved printing systems particularly suited for printing high-density analytical arrays.

SUMMARY OF THE INVENTION

The invention provides printing systems and methods for depositing small volumes of liquid on solid substrates. These systems and methods are useful with a wide variety of liquids and substrates and offer a wide variety of applications, including the deposition of arrays of analytes, such as chemical and biochemical library arrays.

In one embodiment, the invention provides a printing system comprising a pod, a detachable printing device, a substrate, a positioner and a preservation device, wherein (a) the pod comprises a receptacle for reversibly attaching an attachment portion of the printing device; (b) the printing device comprises a reservoir containing a liquid comprising a predetermined agent and in fluid connection with the reservoir, a capillary comprising an axial bore having proximal and distal openings to ambient pressure and a printing tip comprising the distal opening and which prints the agent on the substrate; (c) the positioner moves the pod relative to the substrate; and (d) the preservation device is within, containing or in contact with the printing device and preserves the capability of the printing device to print the agent on the substrate over long-term storage. Generally, the preservation device provides a deterrent to evaporation of the liquid, such as a hermetic barrier, a refrigerator, a humidifier, a hygroscopic agent, etc. The system may also comprise a detachable ganged plurality of such printing devices.

In another embodiment, the invention provides a printing system comprising a pod, a detachable ganged plurality of printing devices, a substrate and a positioner, wherein (a) the pod comprises a receptacle for reversibly attaching an attachment portion of the printing devices; (b) each of the printing devices comprises a reservoir containing a unique agent and in fluid connection with the reservoir, a capillary comprising an axial bore having proximal and distal openings to ambient pressure and a printing tip comprising the distal opening and which prints the agent on the substrate; and (c) the positioner moves the pod relative to the substrate.

In another embodiment, the invention provides a printing system comprising a wire bonding capillary containing a predetermined agent and comprising an axial bore having proximal and distal openings to ambient pressure and a printing tip comprising the distal opening and which prints the agent. And in a more particular embodiment, the invention provides a printing system comprising a ganged plurality of wire bonding capillaries, each containing a different agent and comprising an axial bore having proximal and distal openings to ambient pressure and a printing tip comprising the distal opening and which prints the agent.

A wide variety of more particular embodiments of these systems are disclosed. For example, in one such embodiment, the capillary bore tapers toward the distal opening of the tip; in another, the system further comprises a motion resistor operatively joined to the capillary and providing an incomplete resistance to motion of the capillary along its longitudinal axis, wherein the resistance may be provided by springs, an elastomeric membrane, the weight of the capillary, etc.; in another, the printing device is of one-piece construction; in another, the system further comprises a register comprising a guide which contacts a registration portion of the printing device, distal to the attachment portion, and moves the tip relative to the substrate; etc.

The invention provides methods of making, using and storing the subject systems including methods for printing liquids comprising agents or analytes on substrates with the printing systems, particularly printing methods which comprise the step of decelerating the capillary to move the liquid through the bore, out the tip and onto the substrate, which method may be effected, for example, by tapping the tip onto the substrate.

DETAILED DESCRIPTION OF PARTICULAR EMBODIMENTS OF THE INVENTION

The following descriptions of particular embodiments and examples are offered by way of illustration and not by way of limitation.

In a first aspect, the invention provides a printing system comprising a pod, a detachable printing device, a substrate, a positioner and a preservation device, wherein (a) the pod comprises a receptacle for reversibly attaching an attachment portion of the printing device; (b) the printing device comprises a reservoir containing a liquid comprising a predetermined agent and in fluid connection with the reservoir, a capillary comprising an axial bore having proximal and distal openings to ambient pressure and a printing tip comprising the distal opening and which prints the agent on the substrate; (c) the positioner moves the pod relative to the substrate; and (d) the preservation device is within, containing or in contact with the printing device and preserves the capability of the printing device to print the agent on the substrate over long-term storage. This system is specifically adapted for long-term storage of the printing device and is amenable to a wide variety of suitable pods, detachable printing devices, substrates, positioners, preservation devices, applications and more particular embodiments.

Suitable pods include any structural member that transfers the positioning of the positioner to the printing device through a receptacle for reversibly attaching an attachment portion of the printing device. For example, the pod may simply be the terminus of a mechanical arm of the positioner with an engaging recess for receiving the proximal (distal from the tip) end of a capillary printing device.

Suitable printing devices include any structural member which combines by fluid connection the requisite reservoir and capillary. For example, the printing device may simply be a capillary comprising a liquid-filled bore having a proximate reservoir portion and terminating at a distal portion comprising the printing tip. Alternatively, the reservoir may comprise a more voluminous non-capillary liquid filled chamber having a relatively larger internal diameter in fluid connection with a capillary comprising the printing tip. The reservoir portion of the printing device is adapted to contain and contains a liquid comprising a predetermined agent. The device may be made of any convenient and compatible material. For example, suitable capillary fabrication material ceramic, silicons, glasses, etc. The printing device is adapted or adaptable to contain, store and/or print a wide variety of liquids, including aqueous liquids, liquids comprising organic polar solvents such as alcohols, DMSO, acetonitrile, etc., nonpolar solvents such benzene, chloroform, etc.

Suitable substrates include any material providing a suitable printing surface, and include sheets of glasses, ceramics, plastics, metals, silicons, acetate, cellulose (paper), etc. The substrate may provide a homogeneous surface or a surface offering differential surface chemistry, topography, etc. For example, the surface may offer predetermined printing sites adapted to receiving, binding, reacting, containing and/or retaining the printing fluid.

Suitable positioners include any device which provides the requisite positioning of the printing device to effect the desired printing sites on the substrate. Frequently, the positioner will provide a first positioning within the two-dimensional plane of the substrate surface and a second positioning perpendicular to the surface to effect contact printing on the surface. The positioner is generally electomechanically operated by a computer controlled robot.

Generally, the preservation device of these systems provides a deterrent to evaporation of the liquid, such that printing can be interrupted for extended periods, such as days, preferably weeks, more preferably months and even years, and then resumed without reloading the printing device. In various embodiments, the systems suffer less than a 50%, preferably less than a 20%, more preferably less than a 5% degradation in printing capacity over the storage period, as measured by subsequent error or misprint frequency, fluid loss, etc., as compared with an otherwise comparable but uninterrupted system. A wide variety of suitable preservation devices may be used. In one example, the device comprises a hermetic barrier, such as a seal on the printing device or a container capable of receiving and housing the printing device, which provides a system that is relatively, preferably substantially, more preferably fully closed to the printing solvent liquid and vapor. These barrier or containment devices may also provide a solvent vapor distributor, such as an absorbent sponge wetted with the solvent of the printing fluid, within the closed system to further minimize evaporation. In another example, the device comprises a refrigerator to cool or preferably freeze the liquid in the capillary of the printing device. In yet another example, the device comprises a hygroscopic agent which is incorporated in the liquid in the capillary and reduces the volatility of the liquid. For example, where the solvent of the liquid is water, suitable agents include glycerol (e.g. 5–95%), salts, etc.

The printing system is adaptable to virtually any application of small volume, high resolution liquid printing. For example, a wide variety of chemical and biochemical libraries may be deposited, including libraries derived from random or directed synthetic schemes, natural products including genetic material, etc. A particular application is the deposition of high density arrays of biochemical reagents or analytes such as polypeptides and polynucleotides (polymers of amino acids and nucleotides, preferably at least 5, more preferably at least 15, more preferably at least 50, more preferably at least 150 monomer units in length), e.g. for effecting solid phase, preferably high throughput solid phase immuno assays and hybridization assays.

More particular embodiments of this system include systems wherein the dimensions and composition of the printing device capillary bore interact with the fluid contained therein to maintain the fluid proximate to the distal opening of the capillary tip. For example, the capillary bore may be tapered, preferably conically tapered toward the distal opening of the tip.

In another more particular embodiment, the system further comprises a motion resistor operatively joined to the capillary and providing an incomplete resistance to motion of the capillary along its longitudinal axis, wherein the resistance may be provided by springs, an elastomeric membrane, the weight of the capillary, etc. Such a motion resistor is especially important to facilitate contact printing on relatively planar or flat surfaces, especially wherein the system comprises a plurality of printing devices which print in concert, wherein the resistor(s) permit simultaneous contact of the printing devices on the surface.

In another more particular embodiment, the printing device is of one-piece construction and/or comprises a wire bonding capillary, described below. The system may also comprise a detachable ganged plurality of printing devices.

In another more particular embodiment, the system further comprises a register comprising a guide which contacts a registration portion of the printing device, distal to the attachment portion, and moves the tip relative to the substrate; etc. A wide variety of registers are provided. A printing system comprising a register may further comprise first and second detachable printing capillaries comprising respective first and second probes, a pod comprising a receptacle for attaching one of the capillaries, a substrate upon which the capillaries deposit the probes, whereupon detachment of the first capillary and attachment of the second capillary after deposition of a first portion of a high density probe array by the first capillary on the substrate, the register is capable of positioning the second capillary at a sufficiently similar position relative to the substrate to permit deposition of a second portion of the array by the second capillary on the substrate. In this system, the capillaries and probes may be different or the same.

In a second aspect, the invention provides a printing system comprising a pod, a detachable ganged plurality of printing devices, a substrate and a positioner, wherein (a) the pod comprises a receptacle for reversibly attaching an attachment portion of the printing devices; (b) each of the printing devices comprises a reservoir containing a unique agent and in fluid connection with the reservoir, a capillary comprising an axial bore having proximal and distal openings to ambient pressure and a printing tip comprising the distal opening and which prints the agent on the substrate; and (c) the positioner moves the pod relative to the substrate. This system provides a wide variety of ways of ganging a plurality of printing devices. In one embodiment, the detachable ganged plurality comprises a block having receptacles or holes for and which laterally constrain each of the printing devices. Alternatively, a rigid or elastomeric band or clamp may be used to gang together the printing devices. In a preferred embodiment, these systems provide analyte-specific dedicated printing devices.

In another embodiment of this aspect of the invention, a one-piece block fabricated from a single material element provides the detachable ganged plurality, increasing the precision, accuracy, repeatability, reliability, speed and permitted densities of spot deposition. Because it is made from a single material element this device is also easier and less expensive to construct and maintain. A wide variety of standard microlithography, micromachining and/or microfabrication methods known to those in the art may be used to construct these devices including injection molding, embossing, etching methods such as deep reaction ionic etching (DRIE), electric discharge machining (EDM), deposition, computer numerical control (CNC) milling, etc. Accordingly, the devices may be manufactured from a wide variety of materials depending on the selected manufacturing method, including plastics such as polycarbonate, polystyrene, polypropylene and PMMA; glasses and/or ceramics; semiconductor material such as silicon; and metals such as stainless steel. The devices may be constructed in a variety formats in terms of nozzle density, head size, reservoir size, etc. Print precision and accuracy are provided by precision engineering specifications including: nozzle surface (e.g. flatness) variation of less than 10, preferably less than 5, more preferably less than 2, more preferably less than 1 um across all the nozzle tips of a head and internozzle print volume and distance (center-to-center) variation of less than about 4, preferably less than about 2, more preferably less than 1, more preferably less than 0.5%. The nozzles may be spaced to provide direct loading from standard microtiter sample plates (e.g. 9 mm center-to-center) or at higher densities wherein the reservoirs may be loaded with conventional microvolume liquid handling devices. In a particular embodiment, the nozzles are spaced to correspond with the desired array density, avoiding the need for off-set printing.

In a third aspect, the invention provides a printing system comprising a wire bonding capillary containing a predetermined agent and comprising an axial bore having proximal and distal openings to ambient pressure and a printing tip comprising the distal opening and which prints the agent. Wire bonding capillaries are adapted from semiconductor manufacturing, where a wire bonding process is used to electrically connect metal bond pads formed on a semiconductor die to the leadfingers of a leadframe. In this process, a bond wire is threaded through a wire bonding capillary and the end of the wire protruding through the capillary tip is heated to a molten ball. The molten ball is then mechanically pressed by the bonding capillary against the heated bond pad to alloy the metallic elements of the wire and bond pad. The capillary is then moved to a bonding site on the designated leadfinger where the wire is pressed against the heated leadfinger to bond the wire, then tensioned and sheared. Wire bonding capillaries are well known in the semiconductor manufacturing art, are the subject of numerous publications and patents (see e.g. U.S. Pat. Nos. 3,894,671; 4,877,173; 5,082,154; 5,558,270; 5,662,261) and are commercially available from a number of sources (e.g. Micro-Swiss of Kulicke & Soffa Industries, Inc., Willow Grove Pa., Gaiser Tool Company, Ventura, Calif., Small Precision Tools, Petaluma, Calif., etc.)

In a more particular embodiment, the invention provides a printing system comprising a ganged plurality of wire bonding capillaries, each containing a different agent and comprising an axial bore having proximal and distal openings to ambient pressure and a printing tip comprising the distal opening and which prints the agent.

The invention provides methods of making, using and storing the subject systems including methods for printing liquids comprising agents or analytes on substrates with the printing systems, particularly printing methods which comprise the step of decelerating the capillary to move the liquid through the bore, out the tip and onto the substrate, which method may be effected, for example, by contact printing, e.g. tapping the tip onto the substrate. A wide variety of methods may be used for loading and/or unloading the printing devices, including passive capillary loading and unloading from the printing tip, vacuum-assisted unloading, active pressure purging, etc. Uninterrupted mult-head printing systems comprising 25 20×20 (400 nozzle) heads provide for offset printing 10,000 spot arrays on chip substrates at rates of at least 0.2 chips/sec., preferably 1 chip/sec., more preferably at least 5 chips/sec.

EXAMPLES

Figure 1:
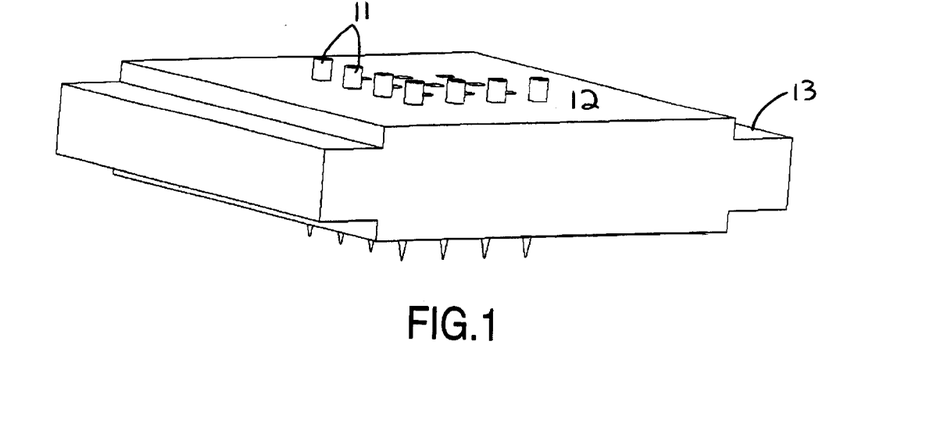
FIG. 1 shows a schematic of a printing head providing a ganged plurality of printing devices.

Referring to FIG. 1, a plurality of printing devices 11 are shown housed in receptacles of a gang 12 comprising tabs 13 for attaching to a pod (not shown) of a printing system.

Figure 2:
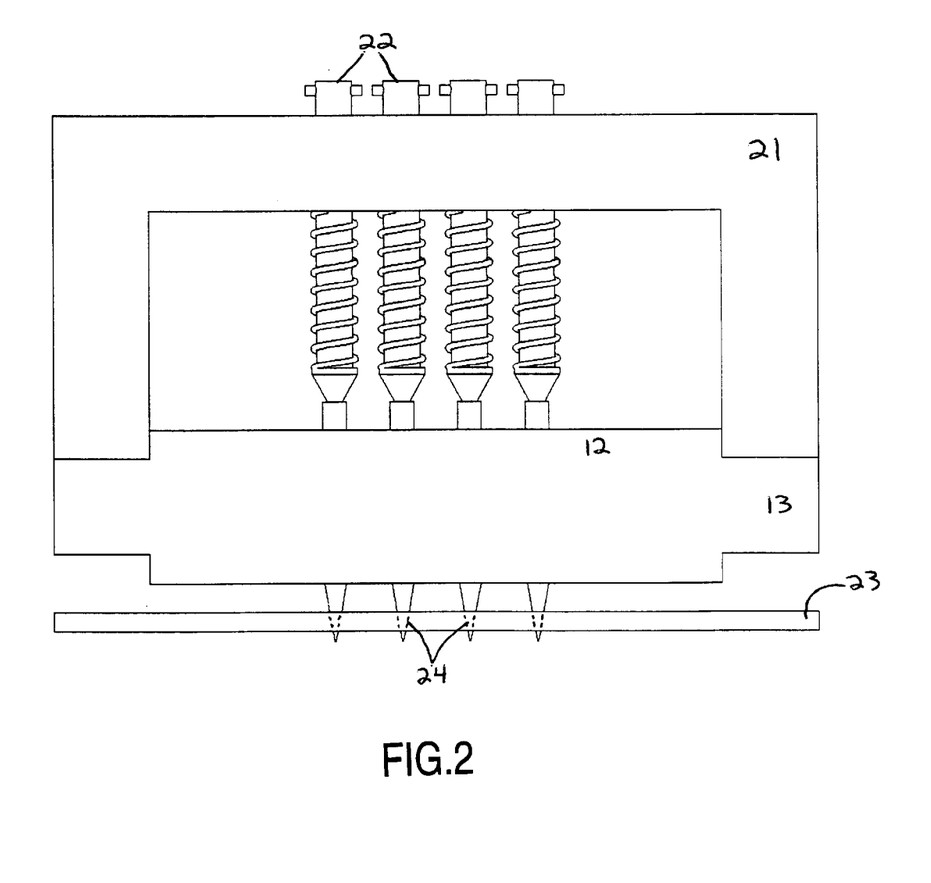
FIG. 2 shows a schematic of a spring block motion resistor, a printing head and a registration plate.

Referring to FIG. 2, a plurality of printing devices 11 are shown housed in receptacles of a gang print head 12 comprising tabs 13. Above the print head 12 is a spring block 21 retaining a plurality of vertical actuators 22. Below the print head 12 is a registration plate 23 comprising a plurality of registration apertures 24.

Figure 3:
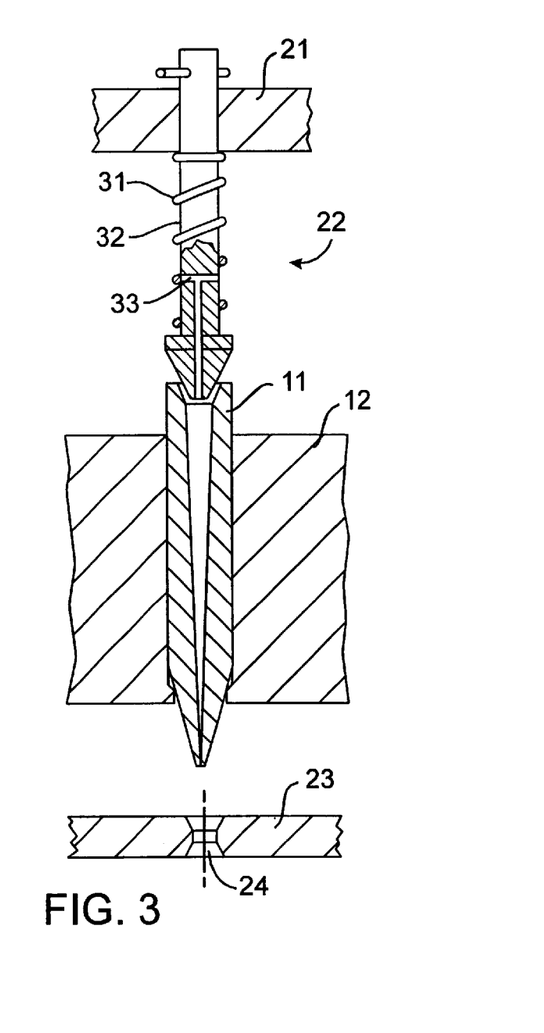
FIG. 3 shows a schematic of a single printing device in the context of spring block motion resistor, printing head and registration plate portions.

Referring to FIG. 3, a printing device 11 is shown housed in a receptacle of a portion of a print head 12. Above the portion of the print head 12 is a portion of a spring block 21 is shown retaining a vertical actuators 22 comprising a spring 31, a spring shaft 32 comprising a vent 33. Below the portion of the print head 12 is a portion of the registration plate 23 comprising a registration aperture 24.

Figure 4:
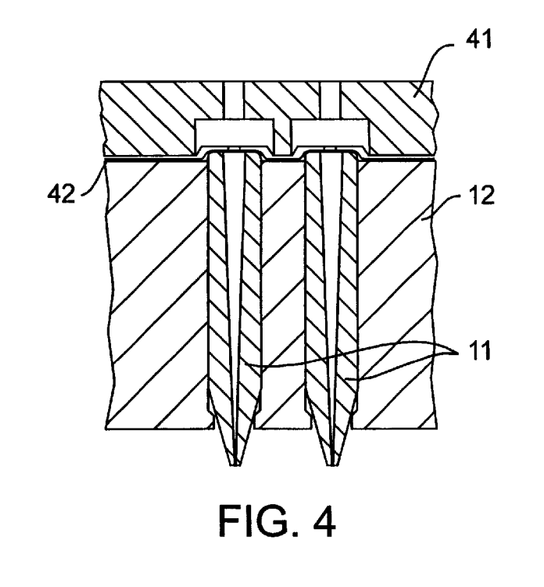
FIG. 4 shows a schematic of a plurality of printing devices in the context of block motion resistor, elastomeric sheet and printing head portions.

Referring to FIG. 4, a plurality of printing devices 11 are shown housed in receptacles of a portion of a print head 12. Above the portion of the print head 12 is a spring and vent cavity block 41 and between the block 41 and the print head 12 is a punch vented latex spring sheet 42.

Figure 5:
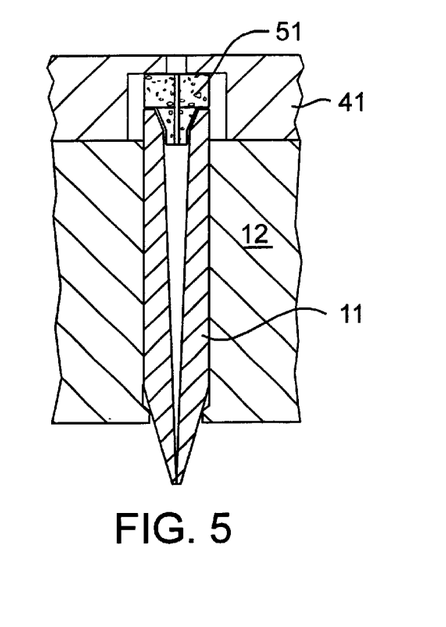
FIG. 5 shows a schematic of a single printing device in the context of foam plug spring block motion resistor and printing head portions.

Referring to FIG. 5, a printing device 11 is shown housed in a receptacle of a portion of a print head 12. Above the portion of the print head 12 is a portion of a spring and vent cavity block 41 is shown retaining a quick-recovery open cell foam spring/vent combination 51.

Figure 6:
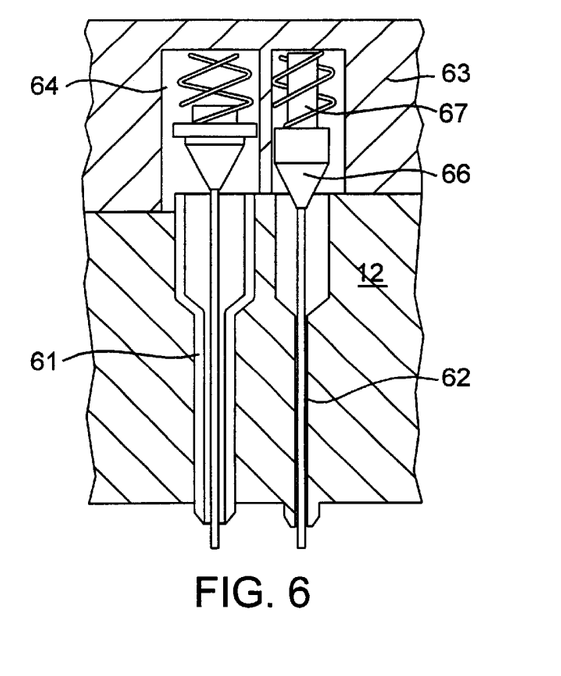
FIG. 6 shows a schematic of an inserted capillary printing device and a machined in printing device in the context of plunger-bearing spring block motion resistor and printing head portions.

Referring to FIG. 6, an inserted capillary printing device 61 and a machined in printing device 62 are shown housed and formed, respectively, in receptacles of a portion of a print head 12. Above the portion of the print head 12 is a spring block 63. The spring block 63 contains spring-loaded plungers 64, each comprising a spring 65, a flange 66 and a shaft 67, and positioned above the printing devices 61 and 62.

Figure 7:
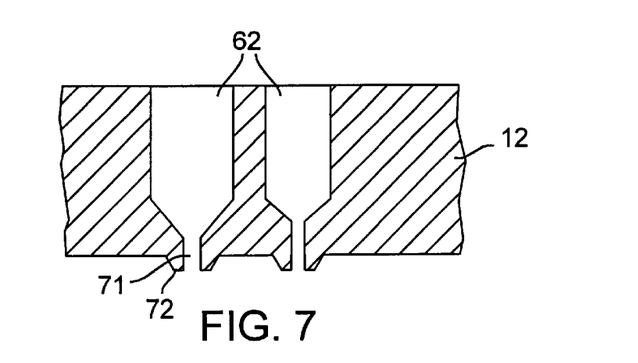
FIG. 7 shows a schematic of a printing head portion having compressable channel walls.

Referring to FIG. 7, a plurality of machined in printing devices 62 are shown formed in receptacles of a portion of a print head 12, wherein the capillary portion 71 of the devices 62 have compressible channel walls 72.

Figure 8:
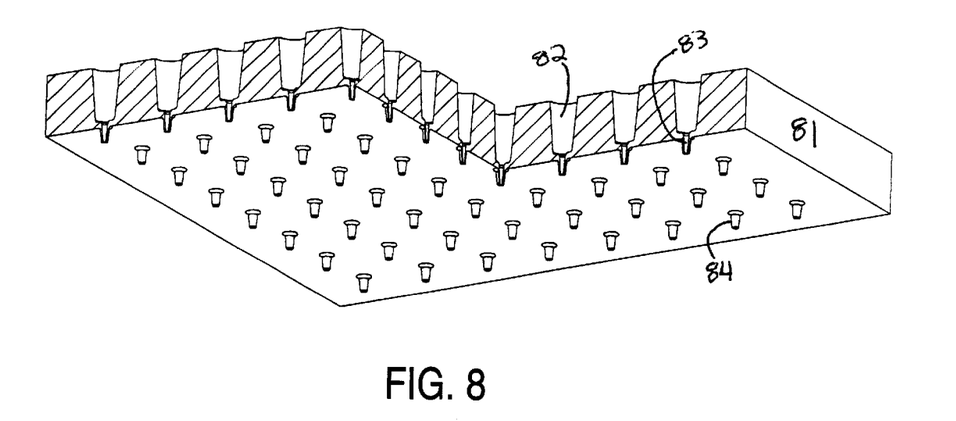
FIG. 8 shows a schematic of a single-piece construction low density multi-chanel printing head.

Referring to FIG. 8, a single-piece construction low density (e.g. 64 tips/cm$^2$) multi-chanel printing head 81 is shown in cross-section. The head 81 comprises injection molded reservoirs 82 in fluid connection with the capillary bores 83 of molded printing tips 84.

Figure 9:
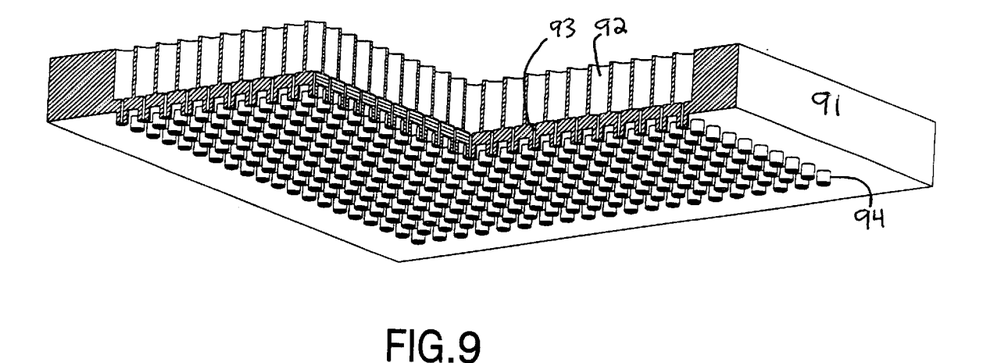
FIG. 9 shows a schematic of a single-piece construction high density multi-chanel printing head.

Referring to FIG. 9, a single-piece construction high density (e.g. 400 tips/cm$^2$) multi-chanel printing head 91 is shown in cross-section. The head 91 comprises etched reservoirs 92 in fluid connection with the capillary bores 93 of etched printing tips 94.

Figure 10:
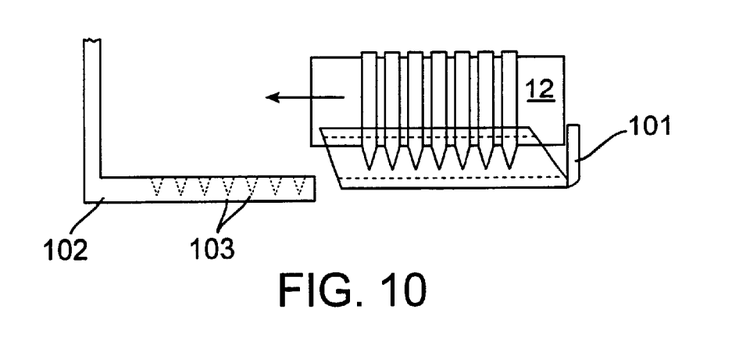
FIG. 10 shows schematic of a registration plate and a printing head comprising a floppy door preservation device.

Referring to FIG. 10, a print head 12 with an operatively affixed closed floppy door preservation device 101 is shown in approach toward a registration plate 102 comprising a plurality of printing tip registration apertures 103.

Figure 11:
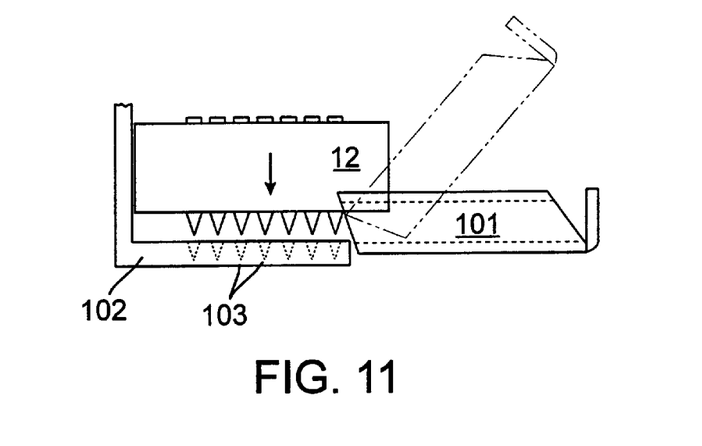
FIG. 11 shows schematic of a registration plate housing a printing head comprising a floppy door preservation device with the door opened.

Referring to FIG. 11, a print head 12 with an operatively affixed open floppy door preservation device 101 is shown in contact with a registration plate 102 comprising a plurality of printing tip registration apertures 103, wherein the open floppy door preservation device 101 is shown in a slide open orientation. In an alternative embodiment, the open floppy door preservation device 101 may be swung open.

Figure 12:
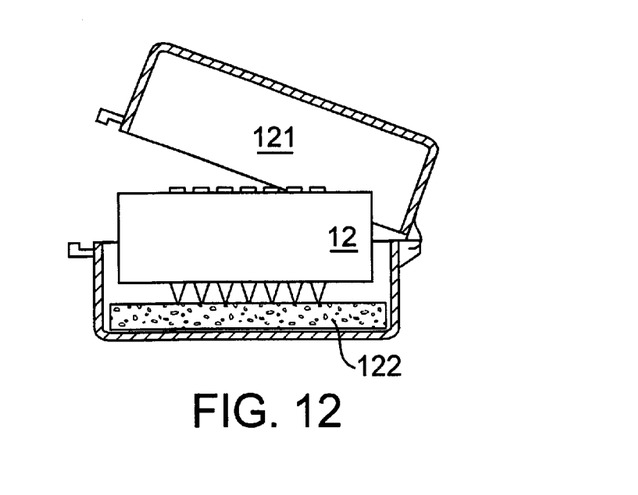
FIG. 12 shows a schematic of an open jewel box type preservation device housing a printing head.

Referring to FIG. 12, an open jewel box type preservation device 121 containing a saturated foam pad 122 is shown housing a print head 12.

Figure 13:
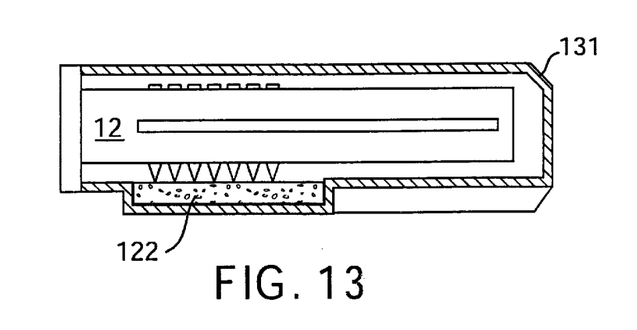
FIG. 13 shows a schematic of a closed caddy box type preservation device housing a printing head.

Referring to FIG. 13, a closed caddy box type preservation device 131 containing a saturated foam pad 122 is shown housing a print head 12.

Figure 14:
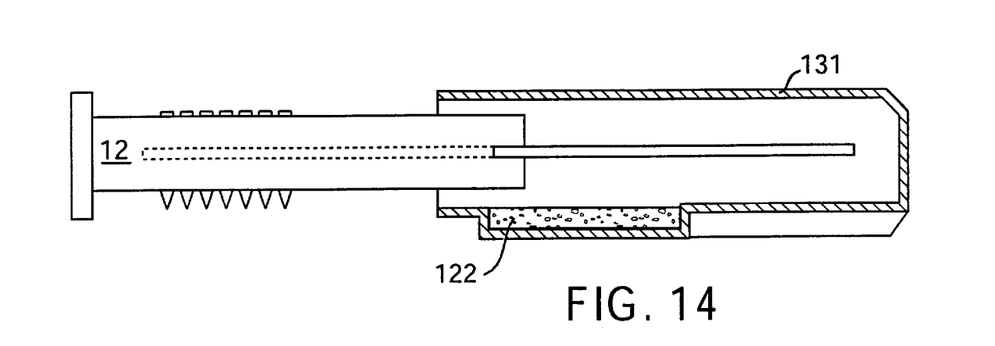
FIG. 14 shows a schematic of an open caddy box type preservation device housing a printing head.

Referring to FIG. 14, an open caddy box type preservation device 131 containing a saturated foam pad 122 is shown housing a print head 12.

Figure 15:
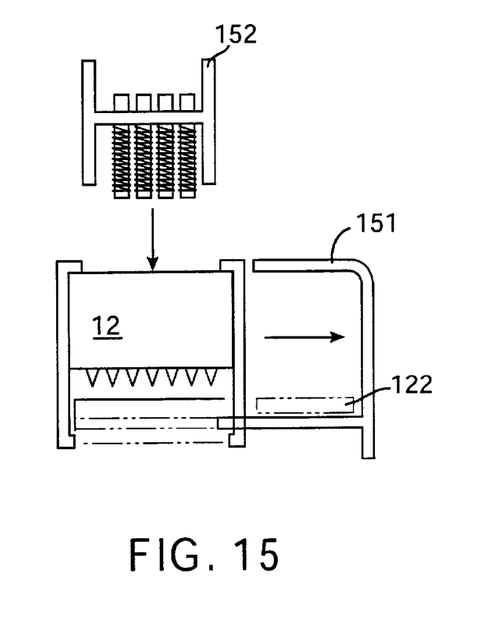
FIG. 15 shows a schematic of a spring block and an open pop-out box type preservation device housing a printing head.

Referring to FIG. 15, a pop-out box type preservation device 151 containing a saturated foam pad is 122 shown in open position housing a print head 12. Above and approaching the print head 12 is shown a spring block 152.

Figure 16:
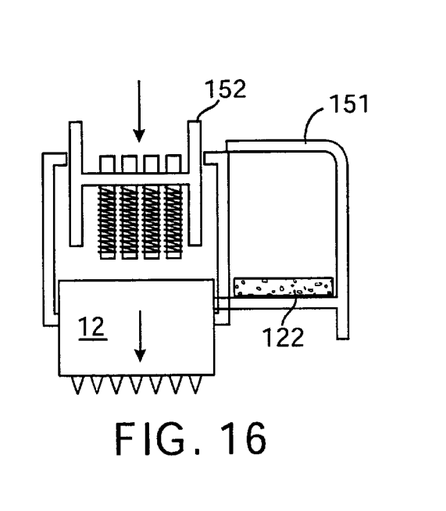
FIG. 16 shows a schematic of a spring block depressing the printing head of an open pop-out box type preservation device.

Referring to FIG. 16, a pop-out box type preservation device 151 containing a saturated foam pad is 122 shown in open position housing a print head 12. Above and depressing the print head 12 is shown a spring block 152.

Figure 17:
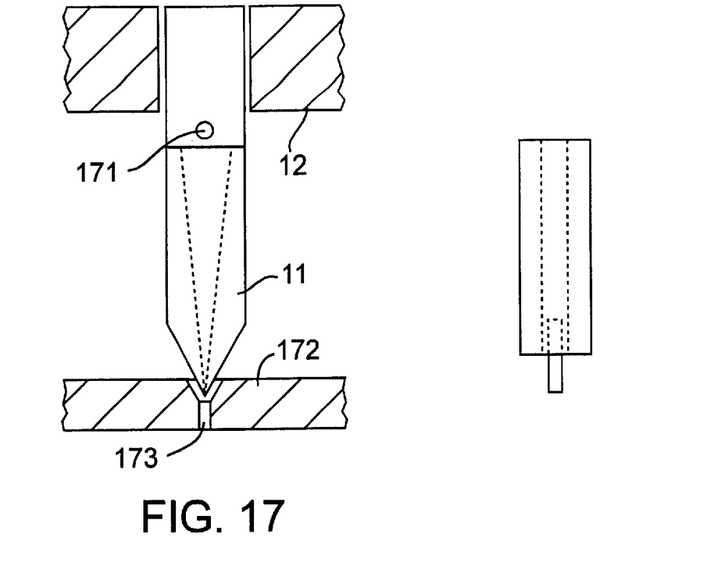
FIG. 17 shows a schematic of a open, passive loading, vaccum evacuation printing tip system.

Referring to FIG. 17, a printing device 11 comprising a vent hole 171 is shown housed in a linear bearing receptacle of a portion of a print head 12. Below the portion of the print head 12 is a portion of a vacuum plate 172 comprising a vacuum aperture 173.

Figure 18:
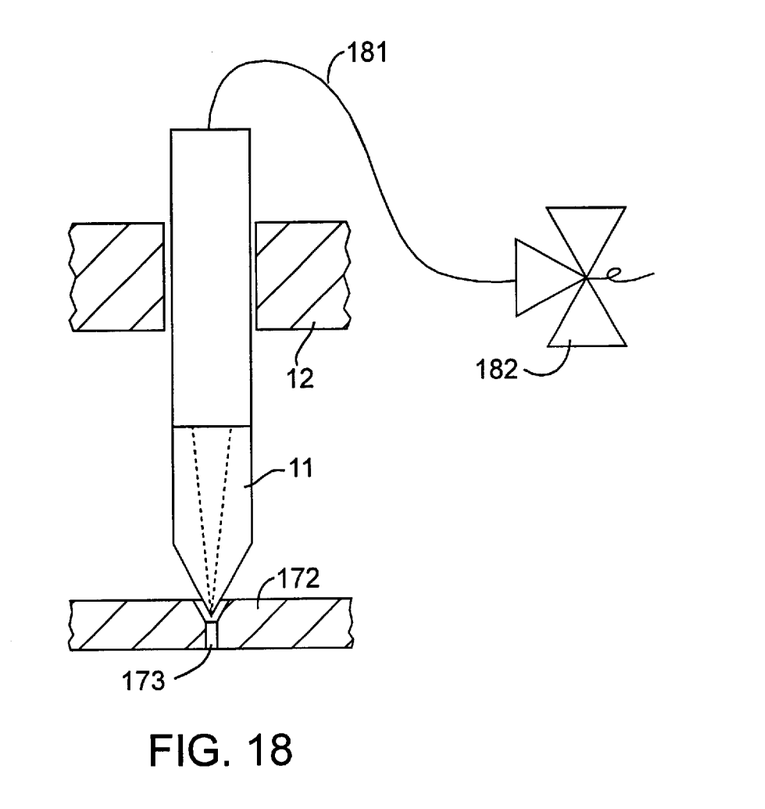
FIG. 18 shows a schematic of a valve-actuated, passive loading, vaccum evacuation, pressure purging printing tip system.

Referring to FIG. 18, a printing device 11 is shown housed in a linear bearing receptacle of a portion of a print head 12. Below the portion of the print head 12 is a portion of a vacuum plate 172 comprising a vacuum aperture 173. In fluid connection with the printing device 11 through tubing 181 is a three-way valve 182 alternatively connecting the device to atmospheric pressure, closure or pressurized nitrogen.

Figure 19:
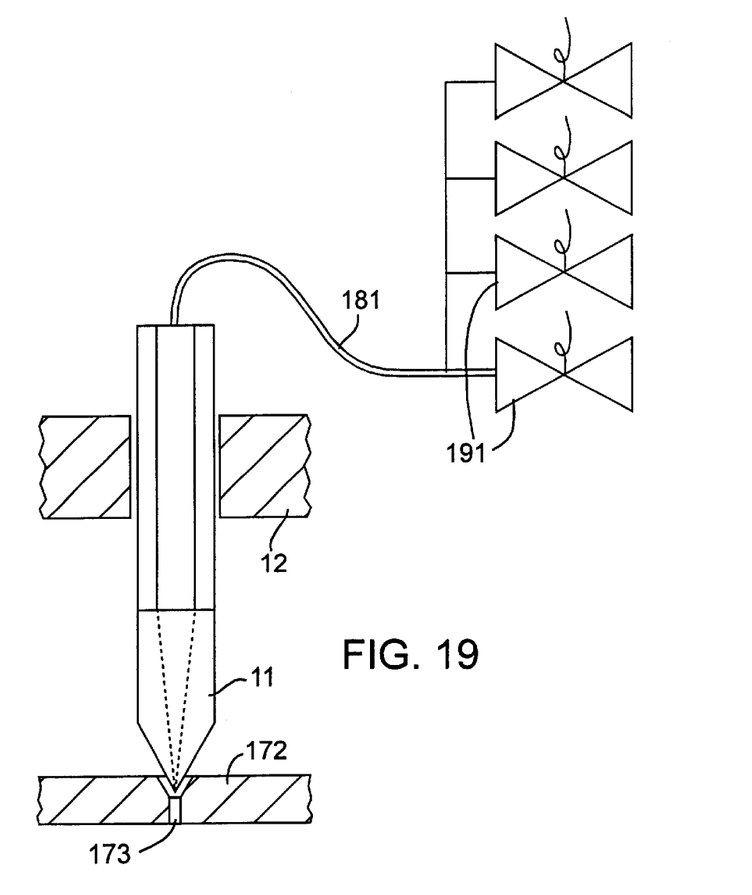
FIG. 19 shows a schematic of a valve-actuated, active loading, vaccum evacuation, pressure purging printing tip system.

Referring to FIG. 19, a printing device 11 is shown housed in a linear bearing receptacle of a portion of a print head 12. Below the portion of the print head 12 is a portion of a vacuum plate 172 comprising a vacuum aperture 173. In fluid connection with the printing device 11 through tubing 181 is are four two-way valves 191 parallel, alternatively connecting the device to closure or respectively, pressurized nitrogen, water, atmospheric pressure and vacuum.

Figure 20:
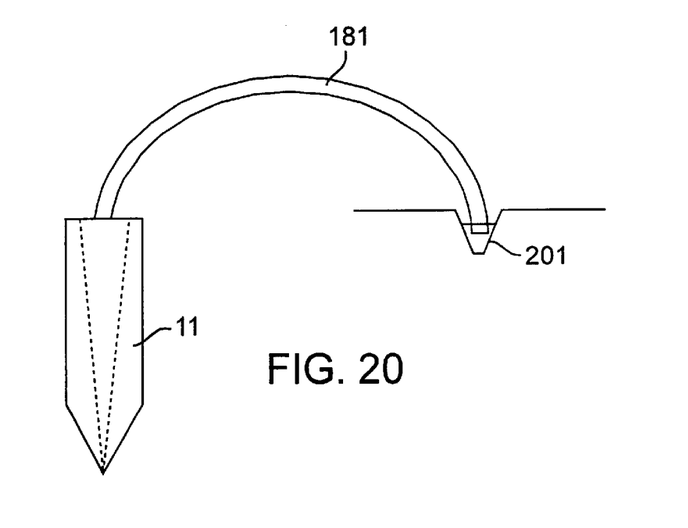
FIG. 20 shows a schematic of a gravity or pressure loading, active purging printing tip system.

Referring to FIG. 20, a printing device 11 is shown in fluid connection through tubing 181 with a sample reservoir 201.

Figure 21:
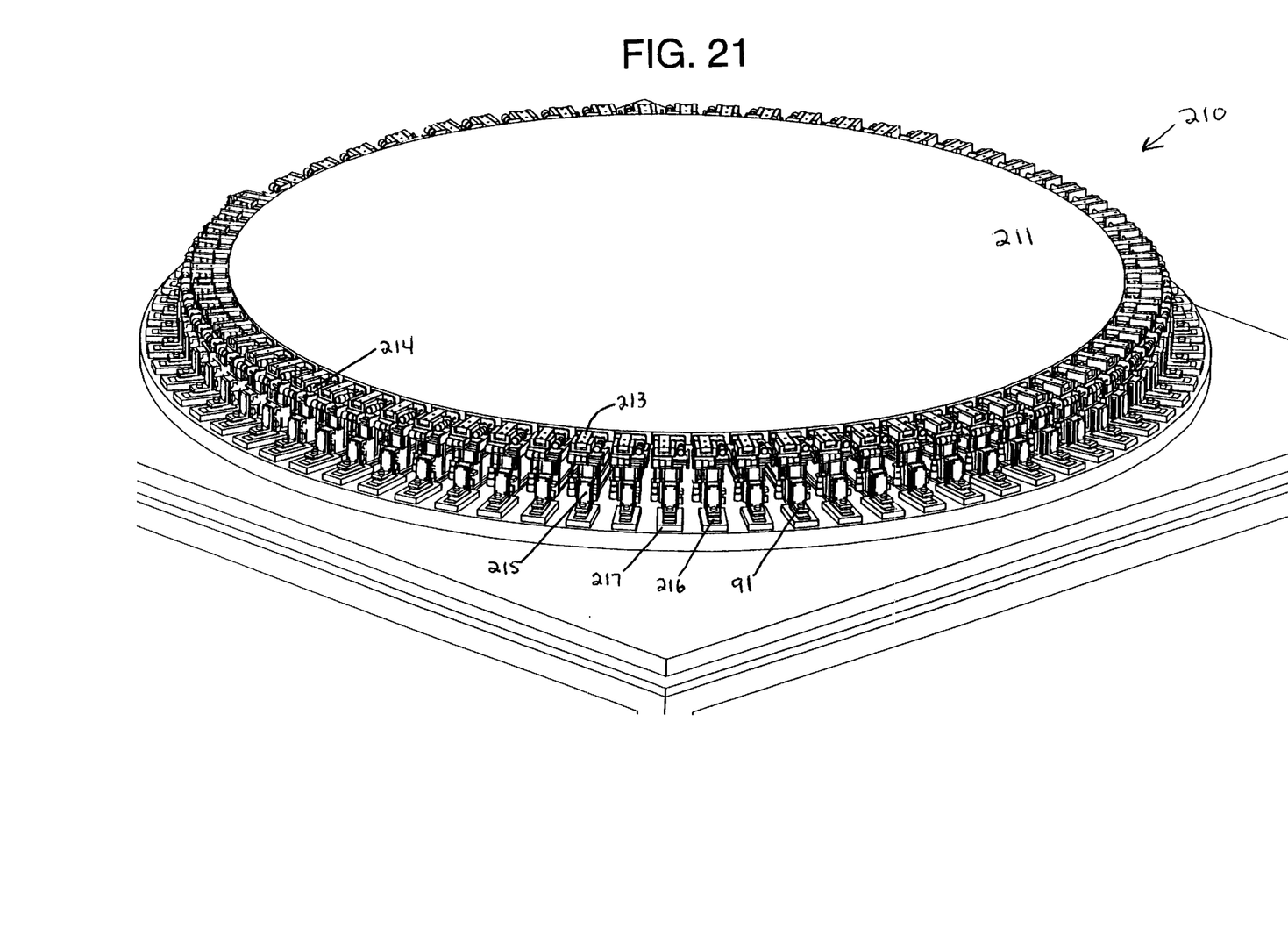
FIG. 21 shows a schematic of a high-throughput a printing system.

Referring to FIG. 21, a printing system 210 comprising a multihead printing assembly 211 rotatably attached to a multichip turntable 212. The assembly 211 comprises a plurality of single-piece construction high density (400 tips/cm$^2$) multi-chanel detachable printing heads 91 joined to the assembly 211 through actuators 213 which provide positioning stages 214 and L-brackets 215 for attaching the print heads 91. The turntable 212 provides chip receptacles 217 which position the chips 216 which provide a printing substrate. In operation, the actuators 213 simultaneously stamp their respective printing heads 91 on the corresponding chips 216. Thereafter, the turntable 212 rotates one chip position and the necessary printing offset is effected by turntable 212 rotation, actuator 213 positioning, or both. As the printing on a given chip 216 is completed (e.g. a complete array is deposited), the chip 216 is removed from the turntable 212 and replaced with a new chip 216, thereby providing uninterrupted printing.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A printing system comprising a pod, a detachable printing device, a substrate, an actuator, and a preservation device, wherein:
   the pod comprises a receptacle for reversibly attaching an attachment portion of the printing device;
   the printing device comprises a reservoir having a proximal opening to ambient pressure, the reservoir containing a liquid comprising a predetermined agent, and a capillary comprising an axial bore having a proximal opening in fluid connection with the reservoir and a distal opening open to ambient pressure, and a printing tip comprising the distal opening operative to print the agent on the substrate;
   wherein the preservation device comprises a hermetic barrier device, the hermetic barrier device being movable between a closed position and an open position, wherein in the closed position the preservation device is operative to preserve the capability of the printing device to print the agent on the substrate over long-term storage of the printing device, wherein in the open position the preservation device is operative to permit coupling of the actuator and the printing device in the printing system,
   wherein the system is operative to print by decelerating the capillary to move the agent through the bore, out the tip and onto the substrate.

2. The printing system of claim 1, wherein the bore tapers toward the distal opening of the tip.

3. The printing system of claim 1 further comprising a motion resistor operatively joined to the capillary and providing an incomplete resistance to motion of the capillary along its longitudinal axis, biasing said motion toward the substrate, wherein the resistor is selected from a plurality of springs, an elastomeric membrane and the weight of the capillary.

4. The printing system of claim 1 further comprising a motion resistor operatively joined to the capillary and providing an incomplete resistance to motion of the capillary along its longitudinal axis, biasing said motion toward the substrate, wherein the resistor is the weight of the capillary.

5. The printing system of claim 1 further comprising a register comprising a guide which contacts a registration portion of the printing device, distal to the attachment portion, and moves the tip relative to the substrate.

6. The printing system of claim 1 wherein the printing device is one of a detachable ganged plurality of printing devices, each comprising a reservoir containing an agent unique to the reservoir.

7. The printing system of claim 1 wherein the printing device is one of a detachable ganged plurality of printing devices, each comprising a reservoir containing an agent unique to the reservoir, wherein the detachable ganged plurality is of one-piece construction.

8. The printing system of claim 1 wherein the printing device is one of a detachable ganged plurality of printing devices, each comprising a reservoir containing an agent unique to the reservoir, wherein the detachable ganged plurality comprises a block having receptacles for and which laterally constrain each of the printing devices.

9. The printing system of claim 1 wherein the printing device is one of a detachable ganged plurality of printing devices, each comprising a reservoir containing an agent unique to the reservoir, wherein the detachable ganged plurality comprises a rigid or elastomeric band or clamp to gang together the printing devices.

10. The printing system of claim 1, wherein the printing device comprises a wire bonding capillary.

11. The printing system of claim 1, wherein the system suffers less than a 20% degradation in printing capacity over the long-term storage.

12. The printing system of claim 1, wherein the agent is a polynucleotide or polypeptide.

13. The printing system of claim 1, wherein the substrate comprises a homogeneous glass surface.

14. The printing system of claim 3 wherein the printing device is one of a detachable ganged plurality of printing devices, each comprising a reservoir containing an agent unique to the reservoir.

15. The printing system of claim 3, wherein the printing device comprises a wire bonding capillary.

16. The printing system of claim 4 wherein the printing device is one of a detachable ganged plurality of printing devices, each comprising a reservoir containing an agent unique to the reservoir, wherein the detachable ganged plurality comprises a block having receptacles for and which laterally constrain each of the printing devices.

17. The printing system of claim 4, wherein the printing device comprises a wire bonding capillary.

18. The printing system of claim 6 wherein the printing device is one of a detachable ganged plurality of printing devices, each comprising a reservoir containing an agent unique to the reservoir.

19. The printing system of claim 6, wherein the printing device comprises a wire bonding capillary.

20. The printing system of claim 16 when the printing device is one of a detachable ganged plurality of printing devices, each comprising a reservoir containing an agent unique to the reservoir.

21. A method for printing an agent on a substrate comprising the step of printing an agent with the printing system of claim 1 by decelerating the capillary to move the agent through the bore, out the tip and onto the substrate.

22. A method for printing an agent on a substrate comprising the step of printing an agent with the printing system of claim 2 by decelerating the capillary to move the agent through the bore, out the tip and onto the substrate.

23. A method for printing an agent on a substrate comprising the step of printing an agent with the printing system of claim 3 by decelerating the capillary to move the agent through the bore, out the tip and onto the substrate.

24. A method for printing an agent on a substrate comprising the step of printing an agent with the printing system of claim 4 by decelerating the capillary to move the agent through the bore, out the tip and onto the substrate.

25. A method for printing an agent on a substrate comprising the step of printing an agent with the printing system of claim 5 by decelerating the capillary to move the agent through the bore, out the tip and onto the substrate.

26. A method for printing an agent on a substrate comprising the step of printing an agent with the printing system of claim 6 by decelerating the capillary to move the agent through the bore, out the tip and onto the substrate.

27. A method for printing an agent on a substrate comprising the step of printing an agent with the printing system of claim 7 by decelerating the capillary to move the agent through the bore, out the tip and onto the substrate.

28. A method for printing an agent on a substrate comprising the step of printing an agent with the printing system of claim 8 by decelerating the capillary to move the agent through the bore, out the tip and onto the substrate.

29. A method for printing an agent on a substrate comprising the step of printing an agent with the printing system of claim 9 by decelerating the capillary to move the agent through the bore, out the tip and onto the substrate.

30. A method for printing an agent on a substrate comprising the step of printing an agent with the printing system of claim 10 by decelerating the capillary to move the agent through the bore, out the tip and onto the substrate.

31. A method for printing an agent on a substrate comprising the step of printing an agent with the printing system of claim 11 by decelerating the capillary to move the agent through the bore, out the tip and onto the substrate.

32. A method for printing an agent on a substrate comprising the step of printing an agent with the printing system of claim 12 by decelerating the capillary to move the agent through the bore, out the tip and onto the substrate.

33. A method for printing an agent on a substrate comprising the step of printing an agent with the printing system of claim 13 by decelerating the capillary to move the agent through the bore, out the tip and onto the substrate.

34. A method for printing an agent on a substrate comprising the step of printing an agent with the printing system of claim 14 by decelerating the capillary to move the agent through the bore, out the tip and onto the substrate.

35. A method for printing an agent on a substrate comprising the step of printing an agent with the printing system of claim 15 by decelerating the capillary to move the agent through the bore, out the tip and onto the substrate.

36. A method for printing an agent on a substrate comprising the step of printing an agent with the printing system of claim 16 by decelerating the capillary to move the agent through the bore, out the tip and onto the substrate.

37. A method for printing an agent on a substrate comprising the step of printing an agent with the printing system of claim 17 by decelerating the capillary to move the agent through the bore, out the tip and onto the substrate.

38. A method for printing an agent on a substrate comprising the step of printing an agent with the printing system of claim 18 by decelerating the capillary to move the agent through the bore, out the tip and onto the substrate.

39. A method for printing an agent on a substrate comprising the step of printing an agent with the printing system of claim 19 by decelerating the capillary to move the agent through the bore, out the tip and onto the substrate.

40. A method for printing an agent on a substrate comprising the step of printing an agent with the printing system of claim 20 by decelerating the capillary to move the agent through the bore, out the tip and onto the substrate.

41. A method for printing an agent on a substrate with a printing system comprising a pod, a detachable printing device, an actuator, a substrate, and a preservation device, wherein:

the pod comprises a receptacle for reversibly attaching an attachment portion of the printing device;

the printing device comprises a reservoir having a proximal opening to ambient pressure, the reservoir containing a liquid comprising a predetermined agent, and a capillary comprising an axial bore having a proximal opening in fluid connection with the reservoir and a distal opening open to ambient pressure and a printing tip comprising the distal opening for printing the agent on the substrate;

the preservation device is within, containing or in contact with the printing device and preserves the capability of the printing device to print the agent on the substrate over long-term storage of the printing device, wherein the preservation device comprises a deterrent to evaporation of the liquid, wherein the deterrent is selected from the group consisting of a hermetic barrier, a refrigerator, a humidifier and a hygroscopic agent, wherein the system is operative to print by decelerating the capillary to move the agent through the bore, out the tip and onto the substrate, said method comprising the steps of:

printing the agent a first time by decelerating the capillary to move the agent through the bore, out the tip;

subjecting the printing device to long-term storage; and without reloading the printing device, printing the agent a second time by decelerating the capillary to move the agent through the bore, out the tip.

* * * * *